United States Patent [19]

Weksler et al.

[11] Patent Number: 5,686,577

[45] Date of Patent: Nov. 11, 1997

[54] T CELL FACTORS INFLUENCING B CELL DEVELOPMENT

[75] Inventors: Marc E. Weksler, Tenafly; Paul Szabo, Linden, both of N.J.

[73] Assignee: Cornell Research Foundation, Inc., Ithaca, N.Y.

[21] Appl. No.: 323,910

[22] Filed: Oct. 17, 1994

[51] Int. Cl.[6] .......................... A61K 38/19; C07K 14/52
[52] U.S. Cl. .................. 530/351; 530/412; 530/417; 424/85.1; 514/2; 514/8; 514/885; 930/140
[58] Field of Search ........................... 530/350, 351, 530/412, 417; 930/140; 514/2, 8, 885; 424/85.1

[56] References Cited

U.S. PATENT DOCUMENTS 5,061,620 10/1991 Tsukamoto et al. ............... 435/7.21
5,159,066 10/1992 Schatz et al. ...................... 536/27

OTHER PUBLICATIONS

Hardy et al., "Resolution and Characterization of Pro–B and Pre–Pro–B Cell Stages in Normal Mouse Marrow," *J. Exp. Med.*, 173:1213–25 (1991).

Li et al., "Regulated Expression of B Lineage Associated Genes During B Cell Differentiation in Bone Marrow and Fetal Liver," *J. Exp. Med.*, 178:951–60 (1993).

Hirano et al. (1986) Nature vol. 326 pp. 73–76.
Rosenberg et al. (1986) Science vol. 223 pp. 1412–1415.
Neale et al. (1992) Mol. Immunol. vol. 29, No. 12, pp. 1457–1466.
Namen et al. (1988) Nature vol. 333 pp. 571–573.
Muegge et al. (1993) Science vol. 261, pp. 93–95.
Faust et al. (1993) J. Exp. Med. vol. 177, pp. 915–923.

*Primary Examiner*—John Ulm
*Assistant Examiner*—Prema Mertz
*Attorney, Agent, or Firm*—Nixon, Hargrave, Devans & Doyle

[57] ABSTRACT

The present invention relates to an isolated protein or polypeptide capable of production by T cells and capable of ultimately activating production of B cells. The present invention further provides an isolated DNA molecule encoding the protein or polypeptide capable of production by T cells and capable of ultimately activating production of B cells. The isolated DNA molecule can be inserted as a heterologous DNA in an expression vector forming a recombinant DNA expression system for producing the protein or polypeptide. Likewise, the heterologous DNA can be incorporated in a cell to achieve this objective. The isolated protein or polypeptide of the present invention can be combined with a pharmaceutically-acceptable carrier or used alone for administration to mammals for activating production of B cells.

5 Claims, 3 Drawing Sheets

T CELL FACTORS INFLUENCING B CELL DEVELOPMENT

The subject matter of this invention was developed with the support of the United States Government (NIH Grant Nos. AG00541 and AG08707).

FIELD OF THE INVENTION

The present invention relates to the development of B cells, more particularly to T cell factor(s) capable of ultimately activating production of B cells.

BACKGROUND OF THE INVENTION

Assembly of immunoglobulin ("Ig") heavy and light chain genes and of $\alpha$ and $\beta$ chain genes of the T cell receptor occurs in developing lymphocytes by somatic recombination. This involves joining separated gene segments to form a complete variable region. The variable region is assembled from V (i.e., variable), J (i.e., joining) and, in some cases, D (i.e., diversity) gene segments in an ordered and highly regulated manner.

Complex mechanisms regulate V(D)J recombination, and these mechanisms are still not well understood. It is known that recombinationally active gene segments are flanked by conserved DNA sequences called joining sequences, which are composed of highly conserved heptamer and nonamer regions which are separated from each other by a spacer region. Davis, M. M., *Annu. Rev. Immunol.*, 3:537-560 (1985).

There are several additional layers of regulation superimposed on restrictions dictated by the joining signals. Developing B and T cells rearrange distinct gene segment families in a well-defined temporal order. Reth et al., *Nature*, 317:353-355 (1985) and Samuelson et al., *Nature*, 315:765-768 (1985). Although different sets of genes are rearranged in developing B and T cells, exogenously introduced T cell receptor gene segments can be efficiently recombined in pre-B cells. This suggests that B and T cell lineages use the same recombination machinery. Yancopoulos et al., *Cell*, 44:251-259 (1986).

The differentiation of lymphocyte stem cells into mature B cells occurs in different organs at various ages. During embryonic life, this process occurs in the liver, in neonates in the spleen, and in adult animals in the bone marrow. Metcalf, D. and Moore, M. A. S., *Hematopoietic Cells: Frontiers of Biology Series*, North Holland Press, Amsterdam, pp. 1-550 (1971).

Immunoglobulin gene rearrangements, i.e., the recombination of the V(D)J or VJ DNA segments during B cell development, require the expression of a set of genes which include the recombination activating genes 1 and 2 ("RAG-1" and "RAG-2," respectively). Schatz et al., "The V(D)J recombination activation gene, RAG-1," *Cell*, 59:1035 (1989) and Oettinger et al., "RAG-1 and RAG-2: Adjacent genes that synergistically activate V(D)J recombination," *Science*, 248:1517 (1990). This process leads to the generation of a diverse B cell repertoire. Translation of the rearranged Ig genes is followed by the expression of immunoglobulin on the surface of B cells. Thereafter, further recombination of the variable Ig gene segments is down-regulated. Tonegawa, S., "Somatic generation of antibody diversity," *Nature*, 302:57 (1983) and Blackwell, T. K. and Alt, F. W., In: *Molecular Immunology*, B. D. Harnes and D. M. Glover, eds., IRL Press, pp. 1-60 (1988). Unfortunately, little is known about the enzymatic machinery that activates RAG gene expression whereby the production of B cells is activated.

RAG mRNA has been detected in the thymus and bone marrow sites in which T or B lymphocytes, respectively, develop antigen receptor diversity. Since mice that lack functional RAG-1 or RAG-2 genes do not rearrange their immunoglobulin or T cell receptor genes, do not produce these gene products and do not develop mature B or T lymphocytes, bone marrow RAG-1 gene activity can be used as an index of the capacity of the bone marrow to generate a diverse B cell repertoire with age. Mombaerts et al., "RAG-1 deficient mice have no mature B and T lymphocytes," *Cell*, 68:869 (1992) and Shinkai et al., "RAG-2 deficient mice lack mature lymphocytes owing to inability to initiate V(D)J rearrangement," *Cell*, 68:855 (1992).

The present invention is directed to the mechanism responsible for B cell production. Use of this mechanism may permit the correction of defects, particularly B cell deficiencies in immune system function and may enhance immune system activity.

SUMMARY OF INVENTION

The present invention relates to an isolated protein or polypeptide capable of production by T cells and capable of ultimately activating production of B cells.

The present invention further provides an isolated DNA molecule encoding the protein or polypeptide capable of production by T cells and capable of ultimately activating production of B cells. The molecule can be inserted as a heterologous DNA in a recombinant DNA expression system to produce the protein or polypeptide. Likewise, the heterologous DNA can be incorporated in a cell to achieve this objective.

The isolated protein or polypeptide of the present invention can be combined with a pharmaceutically-acceptable carrier or used alone for administration to mammals for activating production of B cells.

The isolated protein or polypeptide of the present invention may prove useful, for example, in correcting defects, particularly B cell deficiencies, in immune system function and also may enhance immune system activity.

BRIEF DESCRIPTION OF THE DRAWINGS

FIG. 1A shows the results of a reverse transcription polymerase chain reaction ("RT-PCR") experiment with RNA from spleen cells from three individual mice at each of the ages indicated. Thymic RNA, known to express high levels of RAG-1 mRNA, served as a positive control.

FIG. 4A shows a PCR experiment in which Vh gene recombination in DNA from untreated nude mice (first two lanes) and nude mice injected with activated T cells are compared (second two lanes). Recombination of VJ558, VQ52, V7183 and D segments with J segments was assayed by PCR amplification. Southern blots of the resulting amplified DNA was probed with an ApaI-XbaI genomic J region DNA fragment and the $VDJ_2$ or $DJ_2$ products are indicated for each of the four nude mice. FIG. 4B shows the results of an identical PCR experiment using DNA from bone marrow cells of two young, normal BALB/c mice. The pattern of Vh gene rearrangement is similar to that of nude mice injected with activated T cells.

DETAILED DESCRIPTION OF THE INVENTION

Figure 1A:
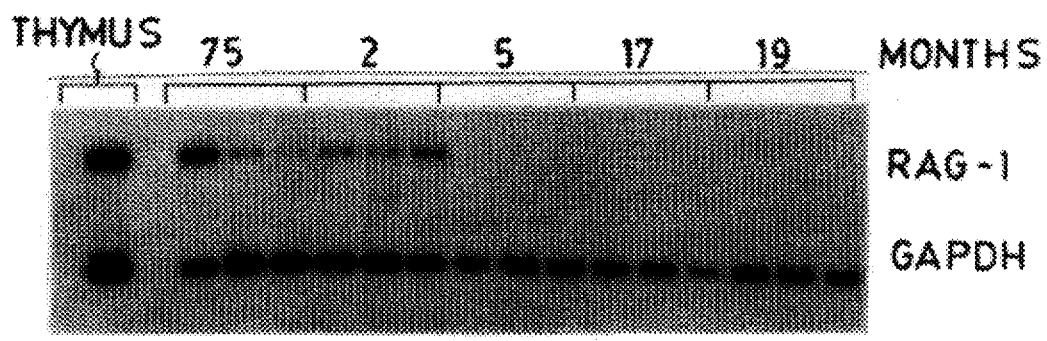
FIGS. 1A and B illustrate the changes in RAG-1 mRNA levels as a function of age in mice.

The present invention relates to an isolated protein or polypeptide capable of production by T cells and capable of ultimately activating production of B cells. The isolated protein or polypeptide has a molecular weight of about 17.5 to 18.5 kilodaltons, preferably 18.0 kilodaltons. It appears to be a secreted protein, a cytoplasmic protein, or a surface protein with its carboxy terminus attached to the outer membrane of a cell. The isolated protein or polypeptide is believed to be capable of (1) activating one or more recombinase activation gene(s), e.g., RAG-1 and RAG-2, (2) activating rearrangement and expression of variable region gene segments, preferably variable heavy region gene segments, more preferably D proximal variable heavy region gene segments, in B cells, and (3) generating a diverse repertoire of B cells.

The protein or polypeptide of the present invention is preferably produced in purified form by conventional techniques. Typically, the protein of the present invention is secreted into the growth medium of recombinant E. coli. To isolate the protein, the E. coli host cell carrying a recombinant plasmid is propagated, homogenized, and the homogenate is centrifuged to remove bacterial debris. The supernatant is then subjected to sequential ammonium sulfate precipitation. The fraction containing the protein of the present invention is subjected to gel filtration in an appropriately sized dextran or polyacrylamide column to separate the proteins. If necessary, the protein fraction may be further purified by high pressure liquid chromatography ("HPLC").

Production of the isolated protein or polypeptide of the present invention is preferably carried out using recombinant DNA technology. An isolated DNA molecule encoding a protein or polypeptide capable of production by T cells and capable of ultimately activating production of B cells can be incorporated in cells. Generally, this involves inserting the isolated DNA molecule into an expression system to which the DNA molecule is heterologous, i.e., not normally present. The heterologous DNA molecule is inserted into the expression system or vector in proper orientation and correct reading frame. The vector contains the necessary elements for the transcription and translation of the inserted protein-coding sequences.

U.S. Pat. No. 4,237,224 to Cohen and Boyer, which disclosure is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/– or KS +/– (see "Stratagene Cloning Systems" Catalog from Stratagene, La Jolla, Calif. (1993), which disclosure is hereby incorporated by reference), pQE, pIH821, pGEX, pET series (see F. W. Studier et. al., "Use of T7 RNA Polymerase to Direct Expression of Cloned Genes," *Gene Expression Technology*, vol. 185 (1990), which disclosure is hereby incorporated by reference) and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., In: *Molecular Cloning: A Laboratory Manual*, 2nd ed., Cold Springs Harbor Laboratory Press, Cold Springs Harbor, N.Y. (1989), which disclosure is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promotors differ from those of procaryotic promotors. Furthermore, eucaryotic promotors and accompanying genetic signals may not be recognized in or may not function in a procaryotic system, and, further, procaryotic promotors are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno (SD) sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which disclosure is hereby incorporated by reference.

Promotors vary in their "strength" (i.e. their ability to promote transcription). For the purposes of expressing a cloned gene, it is desirable to use strong promotors in order to obtain a high level of transcription and, hence, expression of the gene. Depending upon the host cell system utilized, any one of a number of suitable promotors may be used. For instance, when cloning in *E. coli*, its bacteriophages, or plasmids, promotors such as the T7 phage promoter, lac promotor, trp promotor, recA promotor, ribosomal RNA promotor, the $P_R$ and $P_L$ promotors of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promotors produced by recombinant DNA or other synthetic DNA techniques may be used to provide for transcription of the inserted gene.

Bacterial host cell strains and expression vectors may be chosen which inhibit the action of the promotor unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires a Shine-Dalgarno (SD) sequence about 7-9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding a protein or polypeptide capable of production by T cells and capable of ultimately activating production of B cells has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, and the like.

An effective amount of the protein or polypeptide of the present invention can be administered alone or in combination with a pharmaceutically-acceptable carrier to mammals to activate production of B cells.

The isolated protein or polypeptide of the present invention can be administered orally, parenterally, for example, subcutaneously, intravenously, intramuscularly, intraperitoneally, by intranasal instillation, or by application to mucous membranes, such as, that of the nose, throat, and bronchial tubes. The isolated protein or polypeptide may be administered alone or with suitable pharmaceutical carriers, and can be in solid or liquid form such as, tablets, capsules, powders, solutions, suspensions, or emulsions.

The solid unit dosage forms can be of the conventional type. The solid form can be a capsule, such as an ordinary gelatin type containing the protein or peptide of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic acid or magnesium stearate.

The protein or polypeptide of the present invention may also be administered in injectable dosages by solution or suspension of these materials in a physiologically acceptable diluent with a pharmaceutical carrier. Such carriers include sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions.

For use as aerosols, the protein or polypeptide of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

EXAMPLES

The following examples are offered by way of illustration and not by way of limitation.

Example 1—Isolation of Bone Marrow Cells

Female BALB/c and C57BL/6 mice between 3 weeks and 80 weeks of age were obtained from the NIH aging colony (Charles River Laboratories, Wilmington, Mass.). Nude mice were obtained from the Sloan-Kettering Institute (New York, N.Y.). All mice were maintained at the Cornell University Medical College Animal Facilities in laminar flow hoods. Routine serological assays for viral, bacterial and parasitic pathogens were negative. All experiments were performed in accordance with protocols approved by the Animal Care and Use Committee of Cornell University Medical College.

Mice were killed by cervical dislocation. Leg bones were removed, cleaned of adventitious muscle and ligaments and then crushed with a loose teflon dounce and suspended in ice cold Hank's balanced salt solution ("HBSS"). After agitation to wash the cells from the bone fragments, the mixture was allowed to stand for five minutes and the supernatant containing the cells were removed. The cells were collected by centrifugation, washed three times with HBSS, recentrifuged and the pelleted cells resuspended in either guanidinium isothiocyanate solution for the preparation of RNA or HBSS for cell fractionation.

Example 2—Depletion of B Cells from Bone Marrow

Twenty million bone marrow cells were resuspended in supernatant from the rat IgM anti-mouse B220 cell line, ATCC Designation No. TIB-146 (American Type Culture Collection, 12301 Parklawn Drive, Rockville, Md. USA 20852). The cells were incubated on ice for 30 minutes and baby rabbit complement (Cedarlane Laboratories, Hornsby, Ontario, Canada) diluted 1:4 was added and the mixture incubated at 37° C. for 30 minutes. The cells were washed and resuspended in guanidinium isothiocyanate for the preparation of RNA and reverse transcription polymerase chain reaction ("RT-PCR"). Less than 5% of these cells expressed B220 on their cell surface by flow cytometry.

Example 3—RNA and DNA Preparation

Total cellular RNA and DNA were isolated by the guanidinium isothiocyanate CsCl step gradient method of Chirgwin et al., "Isolation of biologically active ribonucleic acid from sources enriched in ribonuclease," Biochemistry, 18:5293 (1979), which disclosure is hereby incorporated by reference. The DNA band at the interface with the 5.7M CsCl cushion was removed and dialyzed against 10 mM Tris, pH 8.0, 1 mM EDTA, deproteinized with proteinase K, extracted with phenol:chloroform and concentrated by ethanol precipitation.

Example 4—Synthetic Oligonucleotide Primers

Oligonucleotide primers for cDNA synthesis and PCR were those used by Chun et al., "The Recombination activating gene-1 (RAG-1) transcript is present in murine central nervous system," Cell, 64:189 (1991), which disclosure is hereby incorporated by reference, and were prepared using an automated DNA synthesizer and cyanoethyl phosphoramidide nucleotide triphosphate precursors. The sequences used were:

a: 5'-CTTGGGAAGT AGACCTGAC-3' (SEQ. ID. NO. 1)

b: 5'-CCAAGCTGCA GACATTCTAG CATC-3' (SEQ. ID. NO. 2)

c: 5'-CAACATCTGC CTTCACGTGA TCC-3' (SEQ. ID. NO. 3)

d: 5'-CAAAGTTGTC ATGGATGACC-3' (SEQ. ID. NO. 4)

e: 5'-CCATGGAGAA GGCTGGGG-3' (SEQ. ID. NO. 5)

Example 5—cDNA Preparation

RAG-1 cDNA was prepared from 5 µg of total cellular RNA by mixing with 200 ng of oligonucleotide primer "a" heated to 68° C. for 5 min. and slowly cooled to 25° C. to anneal the primer. The reaction mixture, 50 µl total volume, consisted of 50 mM TrisCl (pH 8.3), 140 mM KCl, 10 mM $MgCl_2$, 4 mM each dNTP, 25 units RNAasin and 40 units of AMV reverse transcriptase. The reactions were carried out at 42° C. for two hours.

Example 6—PCR Reactions

RAG-1 PCR reactions were prepared in a final volume of 50 µl and contained 1 µl of RAG-1 cDNA reaction, 10 mM TrisCl (pH 8.3), 50 mM KCl, 2 mM $MgCl_2$, 20 mg/ml gelatin, 0.3 mM each dDNP, 125 ng of oligonucleotide primers "b" and "c", 10 µCi of alpha $^{32}P$-dCTP, and 2 units Taq polymerase. Primers "d" and "e", specific for GAPDH mRNA, were included in reactions to serve as a reporter gene for normalizing cDNA input. This is possible because the RAG-1 RT primer shares limited nucleotide homology, 7 and 8 bases at the 3' end of the primer, with the complement of GAPDH mRNA and thus also primed synthesis of GAPDH cDNA. The reaction was heated to 94° C. for 2 min., Taq polymerase was added at 85° C. and this was followed by 25 cycles consisting of 1 min. for annealing at 62° C., 1 min. for extension at 72° C., and 45 sec. at 94° C. for denaturation. Aliquots of the PCR reaction were fractionated on 1.5 or 2% agarose gels; the gels were fixed in 7% TCA for 30 min., dried and exposed to x-ray film. Densitometry was used to quantitate band intensities on films in the linear range of exposure.

Example 7—Rearrangement of Vh Gene Segments

To measure Vh gene rearrangement, PCR reactions were done essentially as described by Costa et al., "Chromosomal position of rearranging gene segments influences allelic exclusion in transgenic mice," Proc. Natl. Acad. Sci. USA, 89:2205 (1992), which disclosure is hereby incorporated by reference, using specific primers for several Vh gene families and a constant J region primer, 5'-GGCTCCCAAT GACCCTTTC TG-3' (SEQ. ID. NO. 6). The 5' end Vh family, J558, is assayed using the specific primer 5'-TCCTCCAGCA CAGCCTACAT G-3' (SEQ. ID. NO. 7); the 3' Vh families Q52, using primer 5'-CTGACCATCA CAAGGACAAC TCCAAGAG-3' (SEQ. ID. NO. 8) and 7183, using primer 5'-AGAGACAATC CCAAGAACAC CCTG-3' (SEQ. ID. NO. 9). Total B cell rearrangements were measured using a primer for the D region, 5'-GTCAAGGGAT CTACTACTGT G-3' (SEQ. ID. NO. 10) from the 5'-flanking recombination signal sequence common to all D regions, and the J region primer. PCR reactions with total bone marrow genomic DNA (1 µg per reaction) and 100 ng of each primer were run for 30 cycles with a program of 1.5 min. at 55° C., 1 min. at 72° C. and 1 min. at 94° C. in a volume of 50 µl. Ten µl of each V(D)J PCR reaction was run on a 2% agarose gel and blotted using standard procedures as described by Sambrook et al., In: Molecular Cloning: A Laboratory Manual, 2nd ed., Cold Spring Harbor Laboratory Press, Cold Spring Harbor, N.Y. (1989), which disclosure is hereby incorporated by reference. The membranes were probed with a $^{32}P$-labeled 2.1 kb ApaI-XbaI fragment from a mouse genomic clone that included the entire $J_1$-$J_4$ region, kindly provided by Dr. M. Nussenzweig (Rockefeller University, New York). Quantitation of band intensity was performed by densitometry.

Example 8—Transfer of Syngeneic T Cells to Nude Mice

A single spleen cell suspension was prepared by teasing the spleen and pressing the preparation through stainless steel grids. The spleen cells were centrifuged, and the pelleted cells washed three times with HBSS and resuspended in medium RPMI 1640 containing 5% FCS at a concentration of $2 \times 10^8$ cells per ml. The suspended splenocytes were loaded onto a nylon wool column and incubated at 37° C. for 1 hour according to Rolink, A. and Melchers, F., "Molecular and cellular origins of B lymphocyte diversity," Cell, 60:1081 (1991), which disclosure is hereby incorporated by reference. The enriched T cell fraction was eluted in RPMI, 5% FCS, washed twice and resuspended at $10^6$ cells per ml in RPMI 1640, 5% FCS. T cells were incubated with PHA at 10 µg/ml for 72 hours at 37° C. The activated T cells were adjusted to a concentration of $2 \times 10^7$ cells/ml and 0.1 ml of the cell suspension or culture supernatant was injected into the tail veins of nude mice.

Example 9—Changes in RAG-1 Gene Expression with Age in C57BL/6 Mice

Figure 1B:
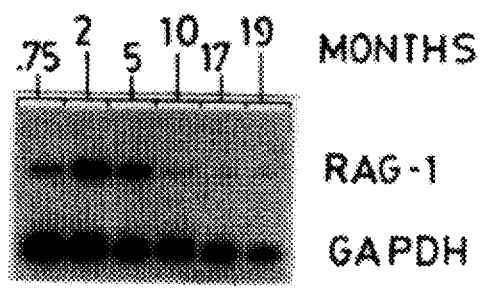
FIG. 1B shows the results of a RT-PCR experiment with RNA from bone marrow from 5 mice at each of the ages indicated.

The level of RAG-1 mRNA was assayed using RT-PCR on cDNA prepared from cells of the spleen, peritoneal cavity and bone marrow from mice 3 to 80 weeks of age. As shown in FIG. 1, RAG-1 mRNA was detected in spleen cells from C57BL/6 mice less than 2 months of age as previously reported by Chun et al., "The Recombination activating gene-1 (RAG-1) transcript is present in murine central nervous system," *Cell*, 64:189 (1991), which disclosure is hereby incorporated by reference. Bone marrow RAG-1 mRNA was detected at low levels in mice three weeks of age and increased 4 to 5 fold to its maximal level by 2 months of age. This level was sustained until the mice were 5 months old. Thereafter, the level of RAG-1 mRNA declined reaching its minimal levels at 10 months of age where it remained. No detectable RAG-1 mRNA was found in peritoneal lymphocytes (data not shown). The same development pattern of RAG-1 mRNA in the spleen and bone marrow cells was observed in BALB/c mice.

Figure 2:
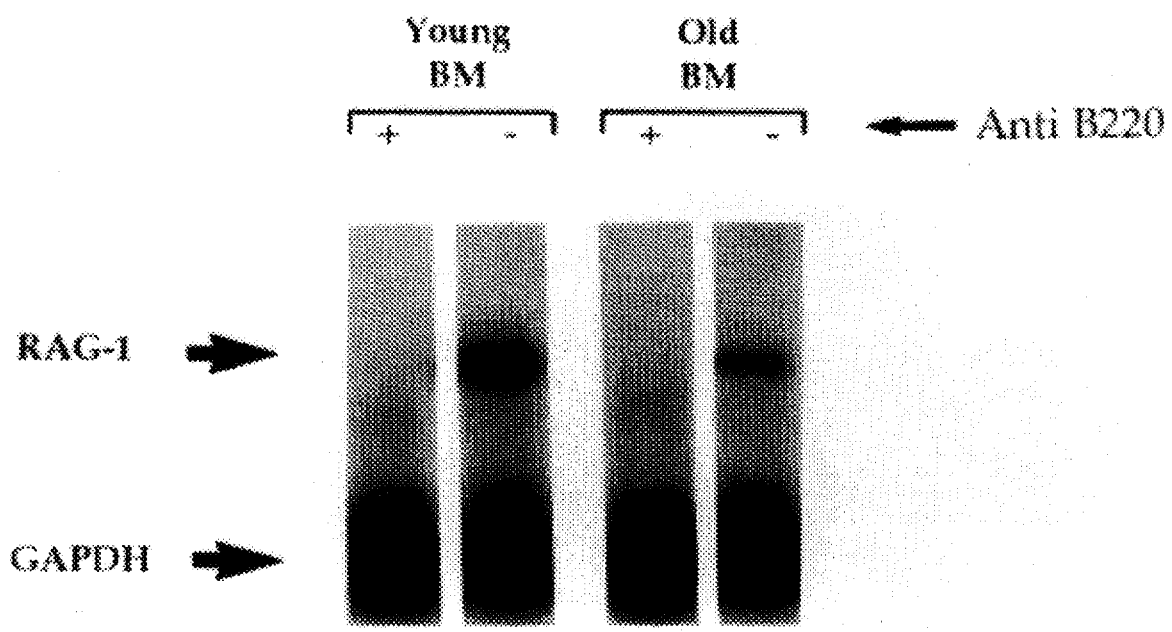
FIG. 2 shows that RAG-1 is expressed in B and pre-B cells via an RT-PCR experiment using RNA prepared from total bone marrow cells of a 6 week old and a 17 month old C57B1 mouse. An aliquot of these cells was treated with (+lanes) or without (-lanes) anti-B220 antibody. All cells were treated with complement.

Example 10—Identification of the Lymphoid Population in Bone Marrow that Expresses RAG-1 mRNA Bone marrow contains lymphoid precursors of both B and T cell lineages. While T cell precursors are known to rearrange their TCR genes and express RAG-1 mRNA within the thymus gland, it was not certain whether all RAG-1 mRNA in the bone marrow could be attributed to B cell precursors. To investigate this question, RAG-1 mRNA was measured in bone marrow cells from young and old mice before and after depleting cells expressing the B220 cell surface marker present on B lymphocytes and their precursors. Fewer than 5% of bone marrow cells treated with antibody to B220 and complement expressed the B220 cell surface marker. RAG-1 mRNA was clearly detectable in the total bone marrow preparation but not in the bone marrow preparations depleted of B cells and their precursors (FIG. 2). Thus, detectable RAG-1 mRNA in bone marrow is expressed by cells of the B but not T lymphocyte lineage.

The decreased level of RAG-1 mRNA in bone marrow cells from old mice might be attributable to a decreased expression of RAG-1 gene by B cell precursors and/or a decreased number of B cell precursors. Published evidence shows that bone marrow B cell precursors are decreased 2 to 3 fold, Riley et al., "B cell precursors are decreased in senescent BALB/c mice but retain normal mitotic activity in vivo and in vitro," *Clin. Immun. Immunopath.*, 59:301 (1991) and Viale et al., "Vh-Gene Family Dominance in Ageing Mice," *Scand. J. Immunol.*, 39:184 (1994), which disclosures are hereby incorporated by reference. Thus, a decreased number of B cell precursors in the bone marrow contributes to the lower expression of the RAG-1 gene in bone marrow cells from old compared to young mice. Additionally, there may be a decreased expression of the RAG-1 gene in B cell precursors from old mice.

Example 11—RAG-1 Expression and Vh Gene Rearrangement in Nude Mice

Figure 3:
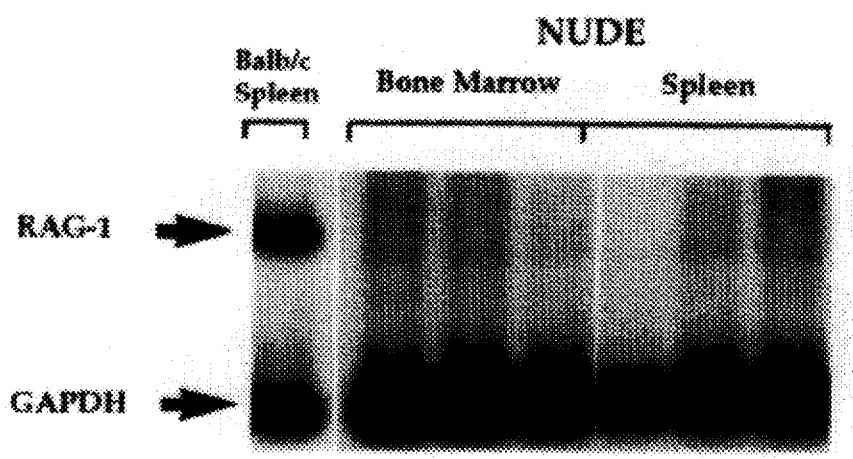
FIG. 3 shows RAG-1 mRNA levels in nude mice via an RT-PCR experiment comparing the RAG-1 mRNA level in total bone marrow and spleen cells of BALB/c nude mice. The first lane from the left is a control reaction using splenic RNA from a 3 week old BALB/c mouse; the size of the authentic RAG-1 PCR product is indicated. The next three lanes are RAG-1 PCR products from total bone marrow RNA of three individual 6 week old BALB/c nude mice. The last three lanes are the PCR products from total splenic RNA of the same mice.

To examine whether decreased thymic gland function influenced RAG-1 gene expression, in the absence of other age-associated changes, the level of RAG-1 mRNA in bone marrow and splenic B cell precursors from both four-eight week old athymic and euthymic BALB/c mice was compared (FIG. 3). BALB/c nude mice exhibited less than 10% the level of RAG mRNA, and Swiss nude mice exhibited less than 20% of level of RAG-1 mRNA seen in normal age matched control mice.

Figures 4A, 4B:
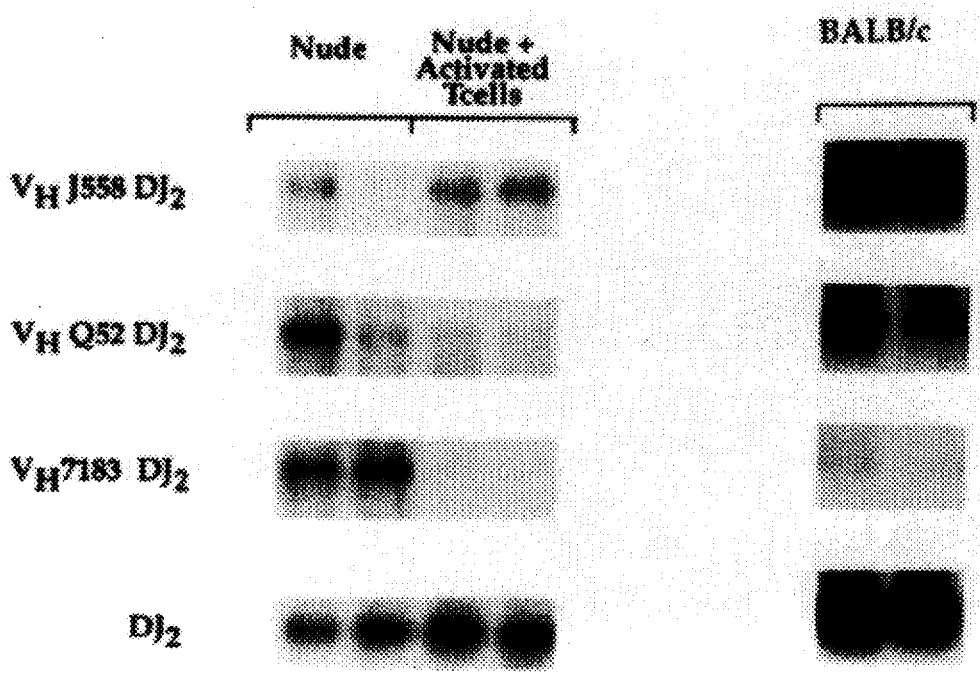
FIGS. 4A–B show the reconstitution of random Vh gene rearrangement in nude mice injected with activated T cells.

Nude mice exhibit other alterations in B cell function including the preferential utilization of D proximal Vh genes, Freitas et al., "Selection of antibody repertoires: transfer of mature T-lymphocytes modifies $V_H$ gene repertoires of athymic mice," *Int. Immunol.*, 1:398 (1989), which disclosure is hereby incorporated by reference. The published reports that nude mice show preferential rearrangement of the D proximal Vh gene families (7183 and Q52) compared to the 5' most Vh gene family, J558, has been extended. Although the absolute level of rearrangements of the J558 Vh gene family varies in different nude mice, as shown in FIG. 4, what should be noted is the ratio between the usage of the 5' J558 gene family and the 3' Vh gene families, Q52 and 7183. As can be seen, this ratio is very much less in nude compared to control animals. Under the conditions used for these PCR reactions, cross-reactivity between the Vh family specific primers and other Vh gene families is limited. Thus, the level of amplified DNA produced reflects the relative number of times a member of a given Vh gene family has been recombined, that is, transposed to the J2 gene segment. Therefore, the level of amplified DNA reflects the potential Vh gene repertoire of the bone marrow B cells in nude mice. A distinct D proximal preference is evident (FIG. 4). As a measure of the number of cells which have rearranged their heavy chain genes, the D and the J region primers were used for PCR to amplify the D gene segment which combines with the J2 segment to form DJ2 segment. The lower level of the PCR product in nude mice suggests that the initiation of Ig gene rearrangement is reduced in the bone marrow of these mice. It is likely that peripheral expansion of the B cells generated in the presence of low level of RAG-1 gene expression leads to a peripheral repertoire which is normal in the number of B cells but not in their clonal diversity.

Figure 5:
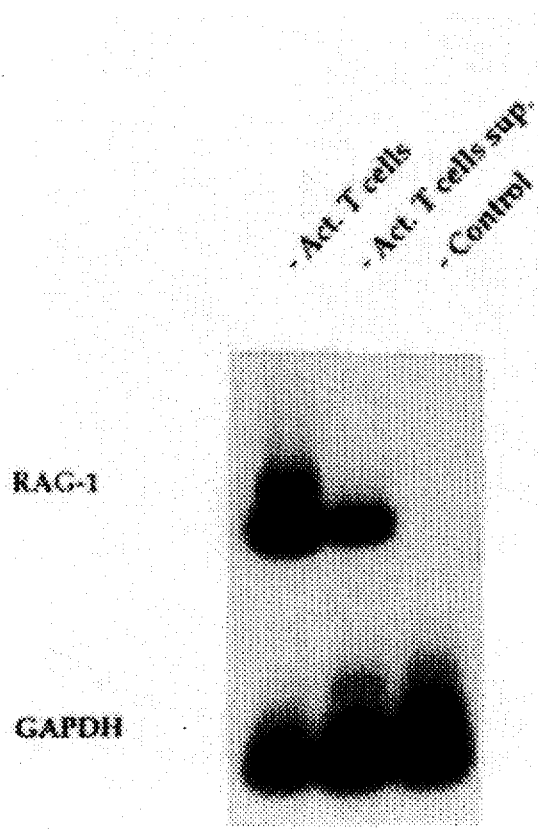
FIG. 5 shows the reinduction of RAG-1 mRNA in bone marrow cells from nude mice injected with activated T cells or tissue culture supernatant of PHA-activated T cells via an RT-PCR experiment in which RAG-1 and GAPDH amplified DNA of bone marrow cell RNA from nude mice injected with PHA-activated T cells (first lane), the supernatant from PHA-activated T cell cultures (second lane) and PHA-containing media as a control (third lane) are compared.

Example 12—Reconstitution of RAG-1 Activity and Random 3' Vh Immunoglobulin Gene Use in Nude Mice Given Activated Syngeneic T Cells or Their Soluble Products Many immune defects in athymic nude mice can be reversed by the injection of T cells from normal syngeneic mice. For this reason, the capacity of PHA-activated splenic T cells from syngeneic, euthymic mice to induce bone marrow RAG-1 mRNA in nude mice was tested (FIG. 5). The activated T cells do not express RAG-1 mRNA and thus do not carry this activity into the nude recipients. The nude mice that received activated T-cells 4–5 days earlier expressed bone marrow RAG-1 mRNA at levels comparable to those seen in age-matched normal mice. Another alteration in B cell maturation observed in nude mice is persistent 3' preferential use of D-proximal Vh genes by B cells in adult mice. This alteration has been reported to be reversed following the injection of T cells, Freitas et al., "Selection of antibody repertoires: transfer of T-lymphocytes modifies $V_H$ gene repertoires of athymic mice," *Int. Immunol.*, 1:398 (1989), which disclosure is hereby incorporated by reference. This finding was confirmed and extended by showing that the injection of activated T cells into nude mice stimulated a random selection of Vh genes. Thus, there was a marked increase in DJ joining and doubling in the usage of the 5' Vh gene family, J558, for rearranged Ig heavy chain genes (FIG. 4). In contrast, the relative use of the 3' Vh gene families Z52 and 7183 decreased by more than 50%. Most interestingly, supernatants from cultures of PHA-activated T cells, but not PHA-containing culture media, stimulated both the induction of RAG-1 mRNA and the random use of Vh genes in the bone marrow of nude mice. The change in the Vh gene use by peripheral B cells, associated with the induction of increased levels of RAG-1 gene expression, suggests that activated T cells or their soluble products acts upon B cell precursors. It is also possible that activated T cells or their soluble products stimulate peripheral expansion of B cells expressing more 5' Vh gene families.

Example 13—Determination of Molecular Weight of the T Cell Factor

The size of the soluble T cell factor was determined analytically by passage of crude factor over a G-75 Sephadex column run in PBS buffer using bovine serum albumin (60 kd), carbonic anhydrase (31 kd) and lysozyme (15 kd) as molecular weight standards to calibrate the column. Pooled eluant fractions were assayed for the induction of RAG-1 mRNA in an in vitro nude mouse bone marrow cell assay. The peak activity corresponded to fractions peaking at 17.5 to 18.5 kd; this molecular weight is in the range observed for other known soluble products of T cells, such as the interleukins.

The rearrangement of immunoglobulin genes occurs in the bone marrow of adult mice and requires the activation of the RAG genes. The level of bone marrow RAG-1 mRNA has been used as an index of the capacity of the bone marrow to support the differentiation of B cell precursors and the diversification of the B cell repertoire with respect to Vh gene usage. It has been demonstrated that the level of RAG-1 mRNA in bone marrow cells increases to a maximum at 2 months of age, is maintained at this level until 5 months of age and then declines to a minimal level by 10 months of age. The age-associated decline in bone marrow RAG-1 mRNA levels might be explained by a decreased expression of the RAG-1 gene by bone marrow B cell precursors and/or a decline in the number of bone marrow cell precursors.

In mammals, B cell development takes place in the bone marrow whose hematopoietic function continues throughout life. For this reason, there is no anatomical "involution" of the bone marrow apparent with age. However, when the expression of RAG-1 mRNA was used to measure the activity of the bone marrow as a site of B cell precursor differentiation, an "involution" of bone marrow immune function occurs at a pace that follows the involution of the thymus gland.

To investigate whether the loss of thymic function is independent of other age-associated changes in the immune system, congenitally athymic, nude mice were studied. Bone marrow RAG-1 mRNA was markedly decreased in BALB/c and Swiss-Webster nude mice. Although the numbers of B cells in nude mice is normal, the documented alteration in Vh gene families use in the B cell repertoire previously reported by Freitas et al., "Selection of antibody repertoires: transfer of T-lymphocytes modifies $V_H$ gene repertoires of athymic mice," *Int. Immunol.*, 1:398 (1989), which disclosure is hereby incorporated by reference, was confirmed. The normal number of B cells despite an impaired maturation of B cell precursors probably results from their peripheral expansion. The impaired expression of RAG-1 gene activity was associated with altered rearrangement of the immunoglobulin Vh gene cluster. Although DJ recombination is comparable in nude and euthymic mice, nude mice are impaired in their recombination of Vh genes distal to the D region of the Vh gene cluster. This raises the possibility that rearrangement of Vh genes distal to the D region may require higher levels of the RAG-1 gene product than do D-proximal Vh genes. This suggests that rearrangement of the Ig cluster is related to the level of RAG-1 gene expression—when the RAG-1 gene product is the limiting, DJ recombination occurs but random V(D)J recombination is impaired. It is also possible that activated T cells or their soluble products could stimulate peripheral expansion of B cells expressing more 5' Vh gene families.

The association between thymic function and RAG-1 gene expression was also supported by the capacity of activated T cells or their products to induce the expression of bone marrow RAG-1 mRNA in nude mice. Furthermore, secreted factor(s) from mitogen-activated T cells also induced the expression of bone marrow RAG-1 mRNA in nude mice. Although the molecular basis of this effect has not been established, IL-7 has been considered a possible candidate as this interleukin has recently been reported to sustain RAG-1 mRNA in thymocytes in culture, Muegge et al., "Interleukin-7: a co-factor for V(D)J rearrangement of the T cell receptor gene," *Science*, 261:93 (1993), which disclosure is hereby incorporated by reference, and is known to stimulate the expansion and differentiation of B cell precursors, Namen et al., "Stimulation of B cell progenitors by cloned murine interleukin 7," *Nature*, 333:571 (1988), which disclosure is hereby incorporated by reference. The activity in the supernatant from activated T cells which induces RAG-1 mRNA in B cell precursors may be distinct from IL-7. First of all, T cells have not been reported to secrete this interleukin and no IL-7 was detectable in T cell supernatants which induced bone marrow RAG-1 mRNA in nude mice. Furthermore, addition of neutralizing antibody to IL-7 to active T-cell supernatants did not alter their capacity to induce RAG-1 mRNA in nude mice (unpublished observations).

In summary, aging is associated with a decline in bone marrow RAG-1 mRNA activity. The decreased expression of RAG-1 gene expression by bone marrow B cells follows the age-associated involution of the thymus gland. Furthermore, the association between impaired thymic function and decreased RAG-1 gene expression by bone marrow B cell precursors was also observed in athymic, nude mice whose bone marrow B cell precursors expressed low levels of RAG-1 mRNA. Finally, transfer of activated T cells or their secreted products to nude mice not only induced RAG-1 mRNA but also corrected the preferential rearrangement of D-proximal Vh genes. These observations provide another mechanism by which the thymus gland mediates the development of a diverse B cell repertoire. Thus, the isolated protein or polypeptide of the present invention could contribute substantially to the correction of defects, particularly B cell deficiencies, in immune system function and may also enhance immune system activity.

Although the invention has been described in detail for the purpose of illustration, it is understood that such detail is solely for that purpose, and variations can be made therein by those skilled in the art without departing from the spirit and scope of the invention which is described by the following claims.

What is claimed is:

1. An isolated protein or polypeptide produced by T cells and having a molecular weight of about 17.5–18.5 kilodaltons, wherein said isolated protein or polypeptide activates production of B cells, activates one or more recombinase activation gene(s), activates rearrangement and expression of variable region gene segments in B cells, and generates a diverse repertoire of B cells.

2. An isolated protein or polypeptide according to claim 1, wherein said protein or polypeptide is purified.

3. An isolated protein or polypeptide according to claim 1, wherein said recombinase activation gene is a RAG-1 gene.

4. An isolated protein or polypeptide according to claim 1, wherein said variable region gene segment is a variable heavy region gene segment.

5. A composition for activating B cell production in mammals comprising:

an isolated protein or polypeptide according to claim 1; and a pharmaceutically-acceptable carrier.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CTTGGGAAGT AGACCTGAC        19

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CCAAGCTGCA GACATTCTAG CATC        24

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CAACATCTGC CTTCACGTGA TCC        23

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CAAAGTTGTC ATGGATGACC        20

( 2 ) INFORMATION FOR SEQ ID NO:5:

( i ) SEQUENCE CHARACTERISTICS:
   ( A ) LENGTH: 18 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:5:

CCATGGAGAA GGCTGGGG    18

( 2 ) INFORMATION FOR SEQ ID NO:6:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:6:

GGCTCCCAAT GACCCTTTCT G    21

( 2 ) INFORMATION FOR SEQ ID NO:7:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:7:

TCCTCCAGCA CAGCCTACAT G    21

( 2 ) INFORMATION FOR SEQ ID NO:8:

( i ) SEQUENCE CHARACTERISTICS:
      ( A ) LENGTH: 28 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:8:

CTGACCATCA CAAGGACAAC TCCAAGAG    28

( 2 ) INFORMATION FOR SEQ ID NO:9:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:9:

AGAGACAATC CCAAGAACAC CCTG    24

( 2 ) INFORMATION FOR SEQ ID NO:10:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear (i i) MOLECULE TYPE: DNA (genomic)

(x i) SEQUENCE DESCRIPTION: SEQ ID NO:10:

GTCAAGGGAT CTACTACTGT G    21